US011576602B2

(12) United States Patent
Takayanagi et al.

(10) Patent No.: US 11,576,602 B2
(45) Date of Patent: Feb. 14, 2023

(54) ELECTROCARDIOGRAM ANALYSIS APPARATUS AND ELECTROCARDIOGRAM SYSTEM

(71) Applicant: NIHON KOHDEN CORPORATION, Tokyo (JP)

(72) Inventors: Tsuneo Takayanagi, Tokyo (JP); Akira Mizuta, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 167 days.

(21) Appl. No.: 16/787,470

(22) Filed: Feb. 11, 2020

(65) Prior Publication Data

US 2020/0260982 A1    Aug. 20, 2020

(30) Foreign Application Priority Data

Feb. 20, 2019    (JP) .............................. JP2019-028720

(51) Int. Cl.
*A61B 5/00*        (2006.01)
*A61B 5/30*        (2021.01)
(Continued)

(52) U.S. Cl.
CPC .............. *A61B 5/303* (2021.01); *A61B 5/316* (2021.01); *A61B 5/339* (2021.01); *A61B 5/7221* (2013.01); *A61B 2560/0276* (2013.01)

(58) Field of Classification Search
CPC ......... A61B 5/303; A61B 5/339; A61B 5/316; A61B 5/7221; A61B 2560/0276
(Continued)

(56) References Cited

U.S. PATENT DOCUMENTS 6,282,440 B1    8/2001    Brodnick et al.
2009/0275805 A1*    11/2009    Lane ..................... A61B 5/02
                                                            600/300
(Continued)

FOREIGN PATENT DOCUMENTS

JP    2001-204701 A    7/2001
JP    2006-180979 A    7/2006
(Continued)

OTHER PUBLICATIONS

Japanese Office Action dated Oct. 11, 2022 issued in Japanese Patent Application No. 2019-028720.

*Primary Examiner* — Erin M Piateski
(74) *Attorney, Agent, or Firm* — Pearne & Gordon LLP

(57) ABSTRACT

An electrocardiogram analysis apparatus includes: an electrocardiogram signal inputting section to which electrocardiogram signals of measurement electrodes attached to a subject are input; a mistaken attachment determining section which, by using the input electrocardiogram signals, determines whether the measurement electrodes are mistakenly attached or not; an outputting section which, if it is determined that the measurement electrodes are mistakenly attached, notifies of mistaken attachment of the measurement electrodes; and an electrocardiogram data storing section which, in a case where there is an input indicative of confirmation of the notification, stores information indicating that the measurement electrodes have been checked, together with the input electrocardiogram signals, and, in a case where there is not an input indicative of confirmation of the notification, stores information indicating that the measurement electrodes have not been checked, together with the input electrocardiogram signals.

9 Claims, 7 Drawing Sheets

(51) Int. Cl.
*A61B 5/316* (2021.01)
*A61B 5/339* (2021.01)

(58) Field of Classification Search
USPC .......................................... 600/509
See application file for complete search history.

(56) References Cited

U.S. PATENT DOCUMENTS

| | | |
|---|---|---|
| 2014/0118138 A1* | 5/2014 | Cobelli ............... A61B 5/4866 340/539.12 |
| 2014/0118166 A1 | 5/2014 | Hampapuram et al. |
| 2015/0250429 A1 | 9/2015 | Hampapuram et al. |
| 2017/0224291 A1 | 8/2017 | Hampapuram et al. |
| 2018/0092568 A1 | 4/2018 | Han et al. |
| 2018/0206798 A1 | 7/2018 | Murai et al. |
| 2019/0059826 A1 | 2/2019 | Hampapuram et al. |
| 2019/0110764 A1 | 4/2019 | Murai et al. |
| 2020/0060630 A1 | 2/2020 | Hampapuram et al. |
| 2020/0138385 A1 | 5/2020 | Hampapuram et al. |
| 2020/0170584 A1 | 6/2020 | Murai et al. |
| 2020/0281541 A1 | 9/2020 | Hampapuram et al. |
| 2020/0305804 A1 | 10/2020 | Hampapuram et al. |
| 2021/0145371 A1 | 5/2021 | Hampapuram et al. |

FOREIGN PATENT DOCUMENTS

| | | |
|---|---|---|
| JP | 2016-502420 A | 1/2016 |
| JP | 2017-018379 A | 1/2017 |
| JP | 2018-510013 A | 4/2018 |

\* cited by examiner

MEASUREMENT ELECTRODES
HAVE BEEN CHECKED

| CHECK | SERIAL NUMBER | NAME | SEX | AGE | DATE OF TEST |
|---|---|---|---|---|---|
| NOT YET | 1234567890 | KOHDEN HANAKO | FEMALE | 45 | 2018/12/14 |
| NOT YET | 1248759630 | KOHDEN TARO | MALE | 73 | 2018/12/14 |
| CHECKED | 1249521781 | KOHDEN KAZUO | MALE | 55 | 2018/12/15 |
| NOT YET | 1251457895 | KOHDEN TETSUYA | MALE | 34 | 2018/12/05 |
| CHECKED | 1251458963 | KOHDEN YUKO | FEMALE | 62 | 2018/12/05 |

ELECTROCARDIOGRAM ANALYSIS APPARATUS AND ELECTROCARDIOGRAM SYSTEM

CROSS-REFERENCE TO RELATED APPLICATIONS

This application is based upon and claims the benefit of priority from prior Japanese patent application No. 2019-028720, filed on Feb. 20, 2019, the entire contents of which are incorporated herein by reference.

TECHNICAL FIELD

The presently disclosed subject matter relates to an electrocardiogram analysis apparatus and electrocardiogram system in which it is possible to see a result of checking whether measurement electrodes are mistakenly attached or not.

BACKGROUND ART

When an electrocardiogram is to be measured, predetermined measurement electrodes must be attached to respective predetermined locations of the subject. However, there may arise a situation where a predetermined measurement electrode is not attached to a predetermined location of the subject, and is mistakenly attached to a location to which another measurement electrode is to be attached.

As disclosed in JP-T-2018-510013, therefore, a technique has been employed in which a possibility that measurement electrodes are mistakenly attached is automatically detected, and the detection result is displayed on a screen or recorded.

In the case where measurement electrodes are mistakenly attached, when an electrocardiogram technician sees a display or record indicating that the measurement electrodes are mistakenly attached, the technician can correct the mistaken attachment of the measurement electrodes, and again measure an electrocardiogram. However, an interpreter who interprets the electrocardiogram, such as a doctor cannot know whether the electrocardiogram technician has measured the electrocardiogram while correctly attaching the measurement electrodes or has measured the electrocardiogram after correcting the mistaken attachments of the measurement electrodes.

In the case where an interpreter performs the interpretation by using an available electrocardiogram, even when the electrocardiogram has been measured while correctly attaching measurement electrodes, there may be a situation where it is suspected that the electrocardiogram has been measured in a state where mistakenly attached measurement electrodes are not corrected. In such a situation, an interpreter cannot know whether such an electrocardiogram waveform is obtained as a result of a non-correction of mistaken attachment of the measurement electrodes, or the measurement electrodes have not been mistakenly attached and the electrocardiogram waveform is original one.

Therefore, it is an object of the presently disclosed subject matter to provide an electrocardiogram analysis apparatus and electrocardiogram system in which it is possible to see a result of checking whether measurement electrodes have been mistakenly attached or not.

SUMMARY OF INVENTION

According to an aspect of the presently disclosed subject matter, there is provided an electrocardiogram analysis apparatus comprising: an electrocardiogram signal inputting section to which electrocardiogram signals of a plurality of measurement electrodes that are attached to a subject are input; a mistaken attachment determining section which, by using the input electrocardiogram signals, is configured to determine whether the measurement electrodes are mistakenly attached or not; an outputting section which, if it is determined that the measurement electrodes are mistakenly attached, is configured to notify of mistaken attachment of the measurement electrodes; and an electrocardiogram data storing section which, in a case where there is an input indicative of confirmation of the notification, is configured to store information indicating that the measurement electrodes have been checked, together with the input electrocardiogram signals, and, in a case where there is not an input indicative of confirmation of the notification, is configured to store information indicating that the measurement electrodes have not been checked, together with the input electrocardiogram signals.

DESCRIPTION OF EMBODIMENTS

Hereinafter, embodiments of the electrocardiogram analysis apparatus and electrocardiogram system of the presently disclosed subject matter will be described while setting the electrocardiogram analysis apparatus as Embodiment 1, and the electrocardiogram system as Embodiment 2.

Embodiment 1

<Configuration of Electrocardiogram Analysis Apparatus>

Figure 1:
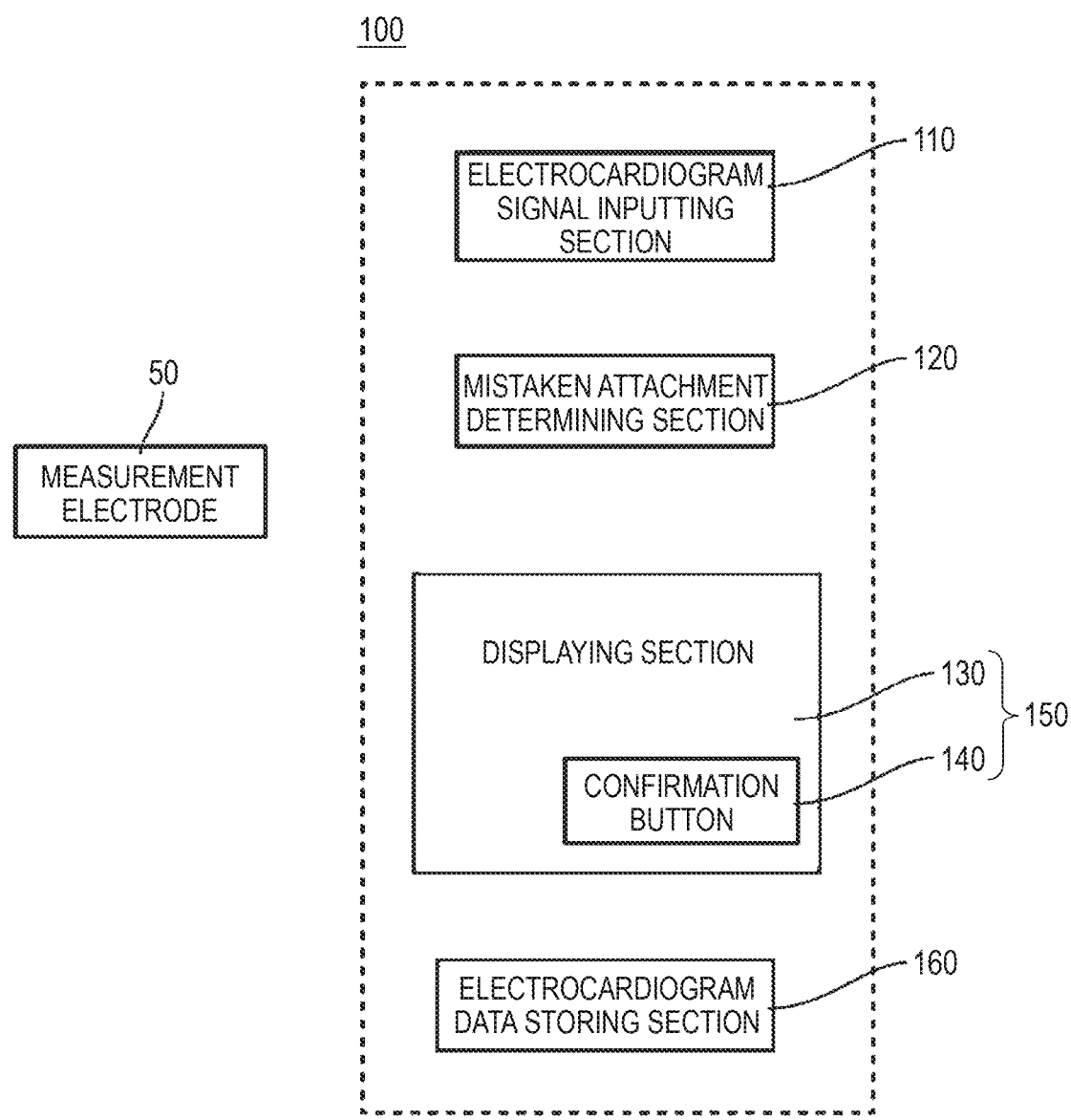
FIG. 1 is a block diagram schematically illustrating the configuration of an electrocardiogram analysis apparatus of Embodiment 1.

FIG. 1 is a block diagram schematically illustrating the configuration of the electrocardiogram analysis apparatus of Embodiment 1. The electrocardiogram analysis apparatus 100 may include an electrocardiogram signal inputting section 110, a mistaken attachment determining section 120, a displaying section 130, and an electrocardiogram data storing section 160. The displaying section 130 displays a confirmation button 140. The displaying section 130 and the confirmation button 140 constitute an outputting section 150.

Electrocardiogram signals of a plurality of measurement electrodes 50 that are attached to the subject are input to the electrocardiogram signal inputting section 110. In the case where a 12-lead electrocardiogram is to be taken, electrocardiogram signals of 10 measurement electrodes 50 in total, i.e., 4 measurement electrodes 50 that are attached to the ankles and wrists of the subject, and 6 measurement electrodes 50 that are attached to the chest are input to the electrocardiogram signal inputting section 110. The measurement electrodes 50 are attached to predetermined locations of the subject, respectively.

The mistaken attachment determining section 120 determines, by using the electrocardiogram signals input from the electrocardiogram signal inputting section 110, whether the measurement electrodes 50 are mistakenly attached or not (whether the possibility that the electrodes are mistakenly attached is higher than a given ratio or not). When one(s) of the measurement electrodes 50 is not attached to the predetermined location(s) of the subject, mistaken attachment of the measurement electrodes 50 occurs. Mistaken attachment of the measurement electrodes 50 is determined by comparing the electrocardiogram signals of the measurement electrodes 50 with electrocardiogram signals that are obtained in the case where the measurement electrodes are correctly attached, or taking a difference between the electrocardiogram signals of the measurement electrodes 50. The technique for determining mistaken attachment may be same as or similar to that disclosed in JP-T-2018-510013, or another related-art technique.

The outputting section 150 is configured by the displaying section 130 and the confirmation button 140, and, if the mistaken attachment determining section 120 determines that the measurement electrodes 50 are mistakenly attached, notifies of the mistaken attachment of the measurement electrodes 50. If, during measurement of an electrocardiogram of the subject, it is determined that the measurement electrodes 50 are mistakenly attached, specifically, the displaying section 130 displays the confirmation button 140. If it is determined that the measurement electrodes 50 are not mistakenly attached, therefore, the displaying section 130 does not display the confirmation button 140. After the mistaken attachment of the measurement electrodes 50 is corrected, the confirmation button 140 is pressed by the electrocardiogram technician. In the above-described example, the confirmation button 140 is displayed on the displaying section 130, but alternatively the confirmation button 140 may be disposed on the apparatus case.

The outputting section 150 further outputs, together with the electrocardiogram signals input from the electrocardiogram signal inputting section 110, information indicating that the measurement electrodes 50 have been checked, or that the measurement electrodes 50 have not been checked. Specifically, the outputting section 150 displays the electrocardiogram signals input from the electrocardiogram signal inputting section 110, as an electrocardiogram on the displaying section 130. In the case where the electrocardiogram technician presses the confirmation button 140 displayed on the displaying section 130, simultaneously, the outputting section 150 outputs information indicating that the measurement electrodes 50 have been checked, and, in the case where the electrocardiogram technician does not press the confirmation button 140 (including the case where the confirmation button 140 has not been displayed), outputs information indicating that the measurement electrodes 50 have not been checked. Therefore, the electrocardiogram technician can notify of the situation where mistaken attachment of the measurement electrodes 50 has been checked, by simply pressing the confirmation button 140 displayed on the displaying section 130.

During interpretation of the electrocardiogram of the subject, the outputting section 150 displays, in a list of test results of a plurality of subjects, information indicating that the measurement electrodes 50 have been checked, or information indicating that the measurement electrodes 50 have not been checked. Therefore, an interpreter such as a doctor can recognize through the list whether the measurement electrodes 50 of each of the subjects have been checked or not. In the list of test results, the situation where the measurement electrodes 50 have been checked, and that where the measurement electrodes 50 have not been checked are displayed by characters, by different colors, or by placing marks in the list. Therefore, the interpreter can recognize at a glance from the list whether the measurement electrodes 50 of each of the subjects have been checked or not.

In the case where there is an input indicative of confirmation of the notification by the outputting section 150, the electrocardiogram data storing section 160 stores information indicating that the measurement electrodes 50 have been checked, together with the input electrocardiogram signals, and, in the case where there is not an input indicative of confirmation of the notification, stores information indicating that the measurement electrodes 50 have not been checked, together with the input electrocardiogram signals. With respect to each of the plurality of subjects together with the input electrocardiogram signals, the electrocardiogram data storing section 160 cumulatively stores information indicating that the measurement electrodes 50 have been checked, or information indicating that the measurement electrodes 50 have not been checked. When, as described above, electrocardiogram signals of the plurality of subjects, and information indicative of checking and not-yet-checking of the measurement electrodes 50 are cumulatively stored, it is possible not only to see the result of checking whether mistaken attachment of the measurement electrodes 50 occurs or not, with respect to each of the subjects, but also to interpret at a glance the check results of the all subjects.

The electrocardiogram analysis apparatus 100 and the various components are configured as described above. Next, the operation of the electrocardiogram analysis apparatus 100 will be described with reference to FIGS. 2 to 8.

<Operation of electrocardiogram analysis apparatus during measurement>

Figure 2:
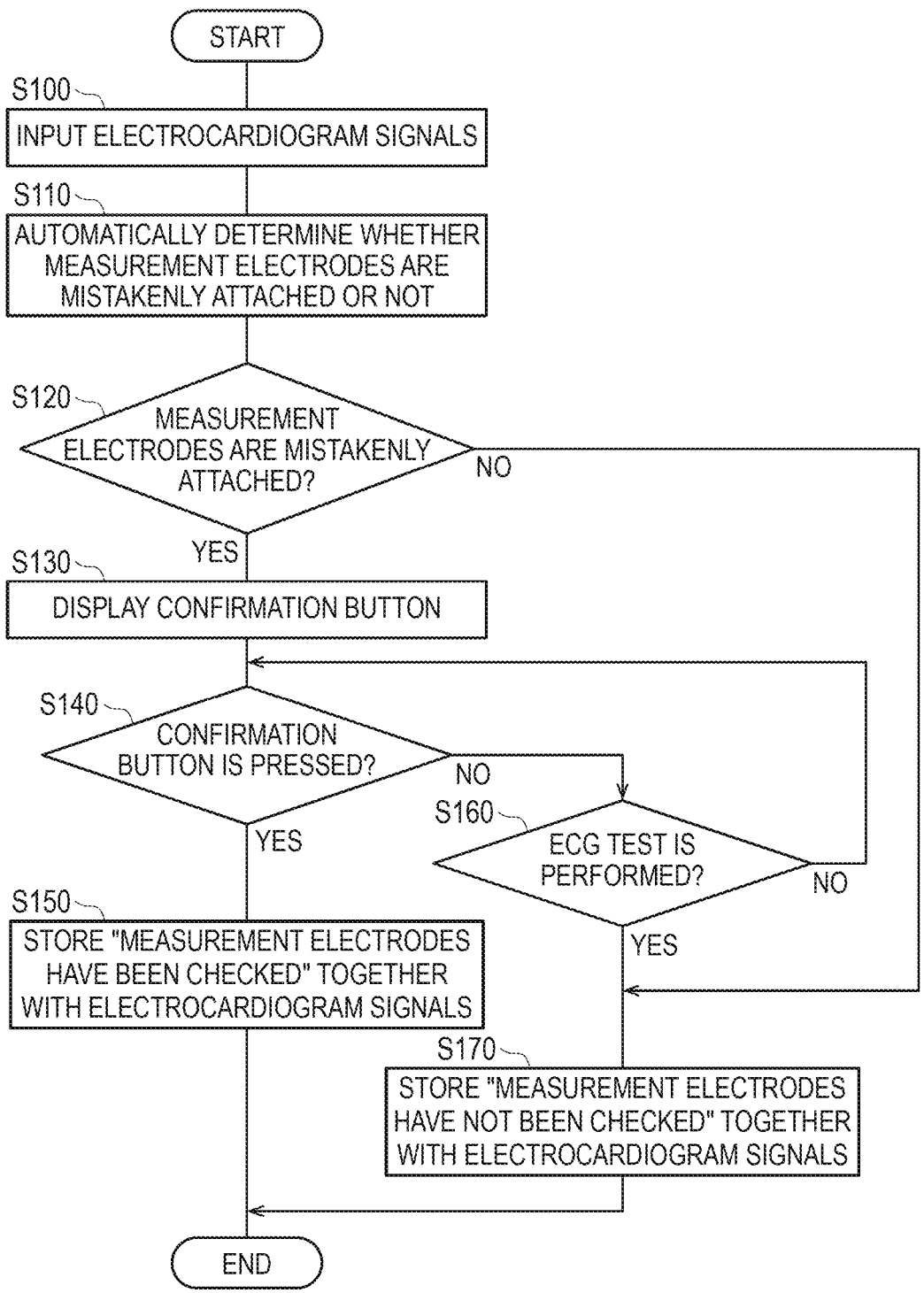
FIG. 2 is a flowchart of operations during measurement in the electrocardiogram analysis apparatus of Embodiment 1.

FIG. 2 is a flowchart of operations during measurement in the electrocardiogram analysis apparatus of Embodiment 1. The electrocardiogram signals of the measurement electrodes 50 that are attached to the subject are input to the electrocardiogram signal inputting section 110 (S100). Next, the mistaken attachment determining section 120 automatically determines whether the measurement electrodes 50 are mistakenly attached or not (S110).

Figure 5:
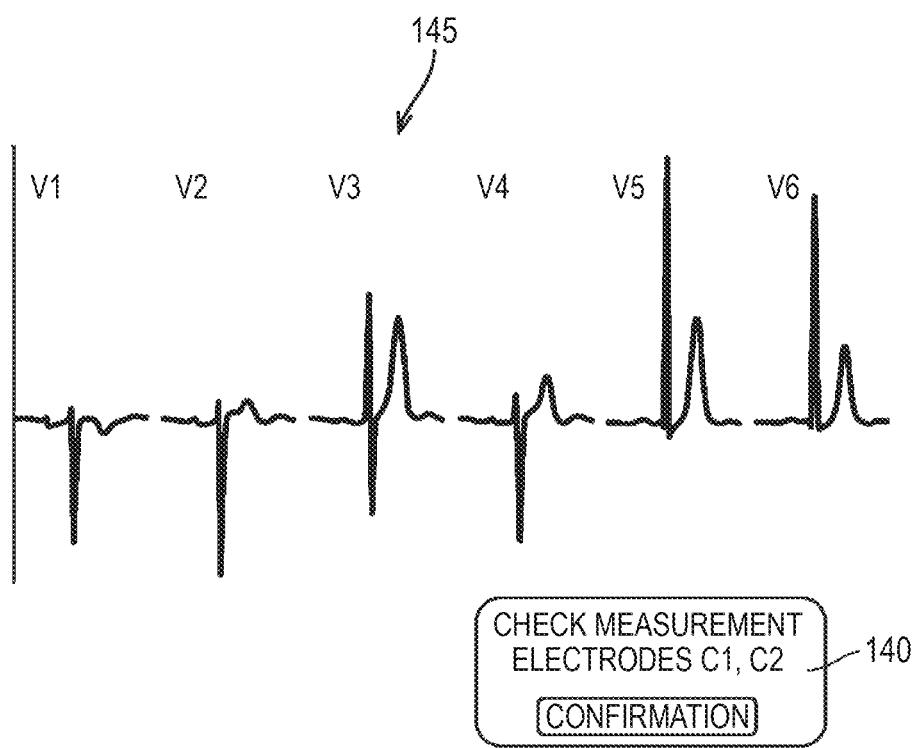
FIG. 5 illustrates a manner of displaying an electrocardiogram and confirmation button that are displayed by a displaying section during measurement.
Figure 6:
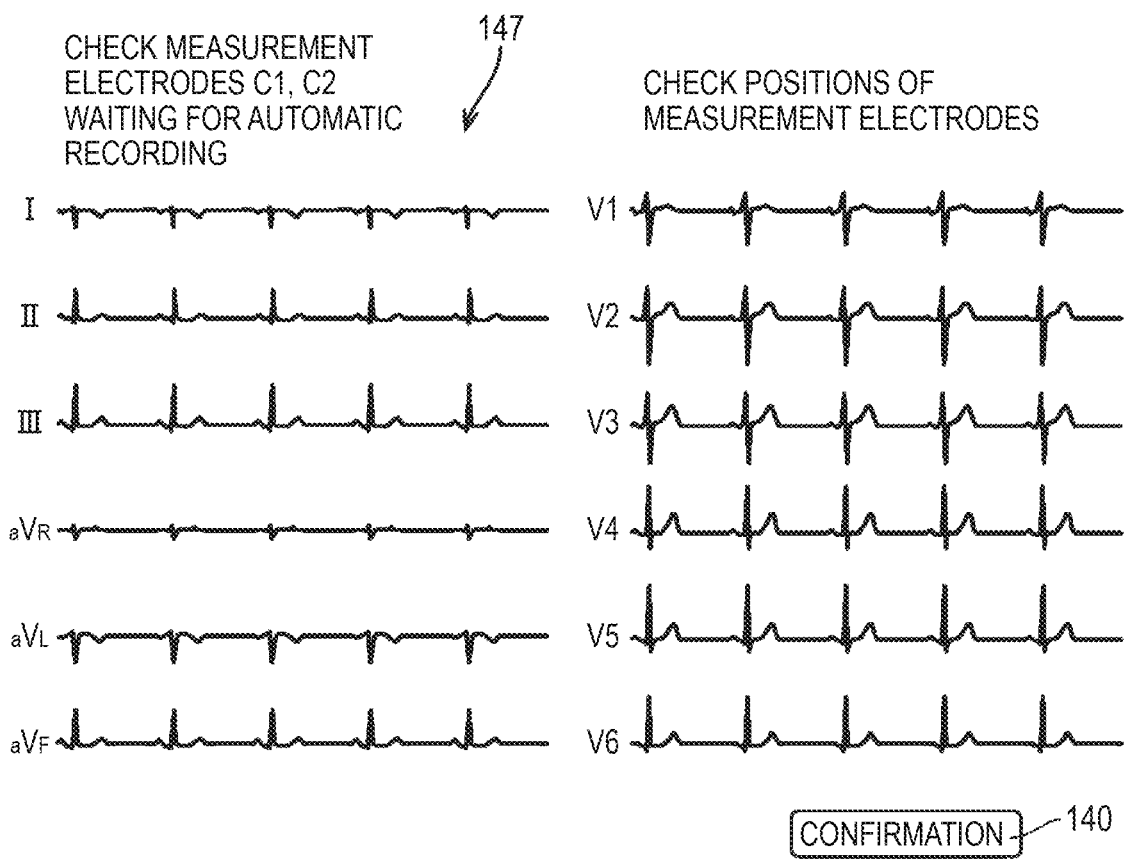
FIG. 6 illustrates another manner of displaying an electrocardiogram and confirmation button that are displayed by the displaying section during measurement.

If the mistaken attachment determining section 120 determines that the measurement electrodes 50 are mistakenly attached (S120: YES), the displaying section 130 displays a confirmation button 140 (S130). Here, FIG. 5 illustrates a manner of displaying an electrocardiogram 145 and confirmation button 140 that are displayed by the displaying section 130 during measurement, and FIG. 6 illustrates another manner of displaying an electrocardiogram 147 and confirmation button 140 that are displayed by the displaying section during measurement. If it is determined that the measurement electrodes 50 are mistakenly attached, the displaying section 130 displays the electrocardiogram 145 supplied from the electrocardiogram signal inputting section 110, and the confirmation button 140 on the screen as illustrated in, for example, FIG. 5. In the case where the measurement electrodes 50 of Channel 1 (C1) and Channel 2 (C2) are suspected to be mistakenly attached, a caution message "Check measurement electrodes C1, C2" is displayed in the confirmation button 140. In the displaying section 130, as illustrated in FIG. 6, alternatively, the displaying section 130 may display the electrocardiograms 147 of all of the measurement electrodes 50, and the confirmation button 140 on the screen. In the alternative, caution messages such as "Check measurement electrodes C1, C2," "Waiting for automatic recording," and "Check positions of measurement electrodes" are displayed above the electrocardiograms 147. If it is determined that the measurement electrodes 50 are not mistakenly attached, the confirmation button 140 and caution messages of FIGS. 5 and 6 are not displayed.

Next, the displaying section 130 determines whether the confirmation button 140 is pressed or not (S140). If the confirmation button 140 is pressed (S140: YES), the electrocardiogram data storing section 160 stores "Measurement electrodes have been checked" together with the electrocardiogram signals (S150). If the confirmation button 140 is not pressed (S140: NO), it is determined whether the ECG test is performed or not (S160). If the ECG test is not performed (S160: NO), the process waits until the confirmation button 140 is pressed. By contrast, if the mistaken attachment determining section 120 determines that the measurement electrodes 50 are not mistakenly attached (S120: NO), or if it is determined that the ECG test is performed (S160: YES), the electrocardiogram data storing section 160 stores "Measurement electrodes have not been checked" together with the electrocardiogram signals (S170). In the case where the measurement electrodes 50 are mistakenly attached, and the confirmation button is pressed, "Measurement electrodes have been checked" is set, and, in the case where the measurement electrodes 50 are not mistakenly attached, or in the case where the measurement electrodes 50 are mistakenly attached, but the ECG test is performed without pressing the confirmation button 140, "Measurement electrodes have not been checked" is set.

<Operation of Electrocardiogram Analysis Apparatus During Interpretation>

Figure 3:
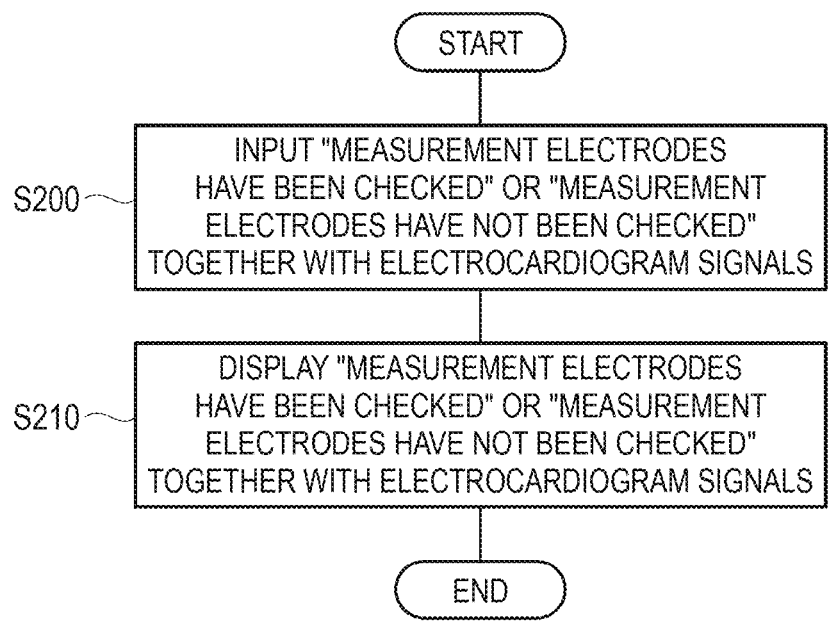
FIG. 3 is a flowchart of operations during interpretation in the electrocardiogram analysis apparatus of Embodiment 1.
Figure 4:
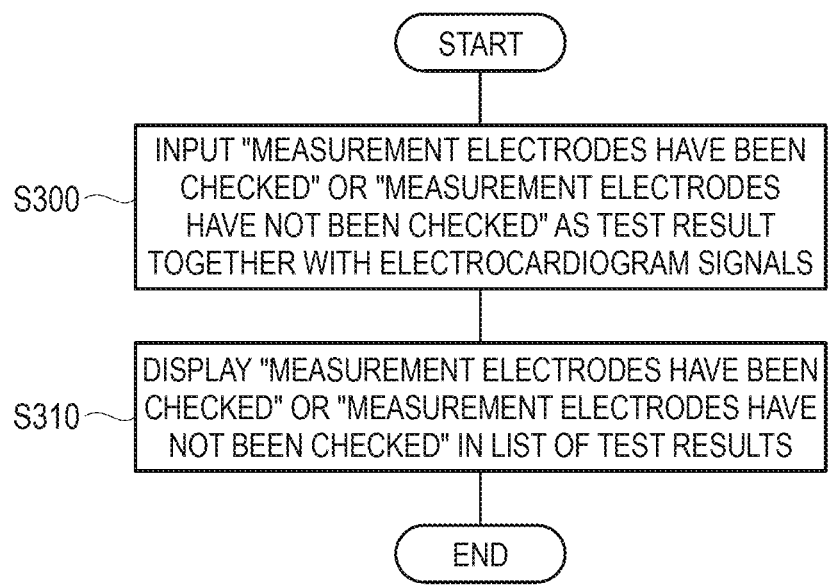
FIG. 4 is another flowchart of operations during interpretation in the electrocardiogram analysis apparatus of Embodiment 1.

FIG. 3 is a flowchart of operations during interpretation in the electrocardiogram analysis apparatus of Embodiment 1, and FIG. 4 is another flowchart of operations during interpretation in the electrocardiogram analysis apparatus of Embodiment 1.

Figures 7, 8:
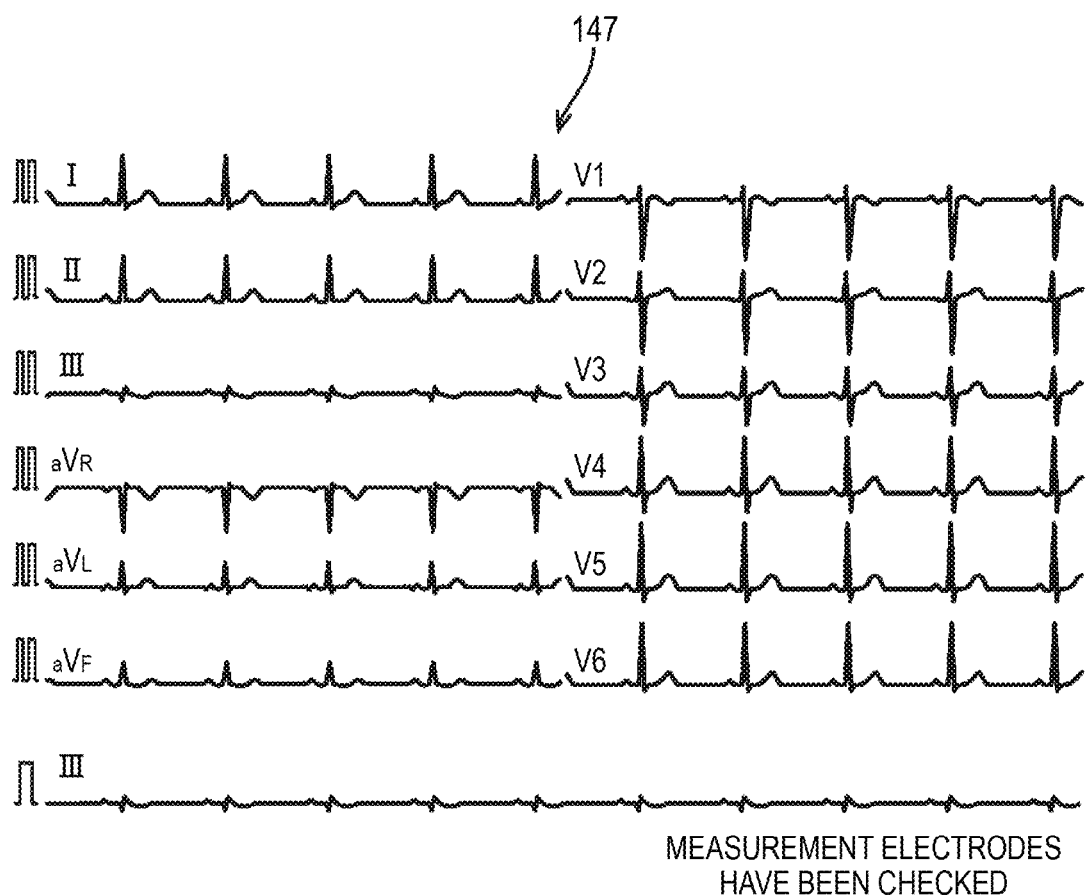
FIG. 7 illustrates a manner of displaying an electrocardiogram that is displayed by the displaying section during interpretation.
FIG. 8 illustrates a manner of displaying a list of subjects that is displayed by the displaying section during interpretation.

"Measurement electrodes have been checked" or "Measurement electrodes have not been checked" is supplied together with the electrocardiogram from the electrocardiogram data storing section 160 to the outputting section 150 (S200). Next, the displaying section 130 displays "Measurement electrodes have been checked" or "Measurement electrodes have not been checked" together with the electrocardiogram signals (S210). FIG. 7 illustrates a manner of displaying an electrocardiogram that is displayed by the displaying section 130 during interpretation. With respect to the electrocardiogram 147 in which mistaken attachment of the measurement electrodes 50 has been checked, as illustrated in FIG. 7, the displaying section 130 displays the electrocardiogram 147, and further displays "Measurement electrodes have been checked" in the lower right side of the electrocardiogram 147. The interpreter such as a doctor sees the display of "Measurement electrodes have been checked," and knows that the electrocardiogram 147 is a reliable electrocardiogram that is measured in a state where the measurement electrodes 50 are not mistakenly attached. The doctor can test the symptom of the patient with confidence in the electrocardiogram 147. With respect to the electrocardiogram 147 in which mistaken attachment of the measurement electrodes 50 is not observed, the displaying section 130 displays "Measurement electrodes have not been checked" in the lower right side of the electrocardiogram 147 in place of "Measurement electrodes have been checked." The doctor sees the display, and knows that the electrocardiogram 147 is a reliable electrocardiogram that is measured in a state where the measurement electrodes 50 are not mistakenly attached.

The displaying section 130 may display test results of a plurality of subjects in the form of a list. In this case, the electrocardiogram data storing section 160 supplies together with the electrocardiogram "Measurement electrodes have been checked" or "Measurement electrodes have not been checked" as a test result, to the outputting section 150 (S300). In the list of test results, the displaying section 130 displays information indicating "Measurement electrodes have been checked" or "Measurement electrodes have not been checked" (S310). FIG. 8 illustrates a manner of displaying a list of subjects that is displayed by the displaying section 130 during interpretation. The displaying section 130 displays test results of the subjects that are cumulatively stored in the electrocardiogram data storing section 160, in the form of a list as illustrated in FIG. 8. In "Check" column of the list, in the case of "Measurement electrodes have not been checked," "Not yet" is displayed, and, in the case of "Measurement electrodes have been checked," "Checked" is displayed. Therefore, the interpreter can recognize from the list which one(s) of the subjects has an electrocardiogram that has been checked, or that has not yet been checked. In the list of test results, the indication that the measurement electrodes 50 have been checked, or that the measurement electrodes 50 have not been checked may be displayed by characters ("Not yet" or "Checked") as in FIG. 8, displayed by different colors (subjects of "Not yet" are highlighted with, for example, gray marker) as in FIG. 8, or displayed by making a mark in the list (subjects of "Not yet" are provided with a symbol such as a check mark or a heart mark). Therefore, the interpreter can recognize at a glance from the list whether the measurement electrodes 50 of each of the subjects have been checked or not.

Embodiment 2

<Configuration of Electrocardiogram System>

Figure 9:
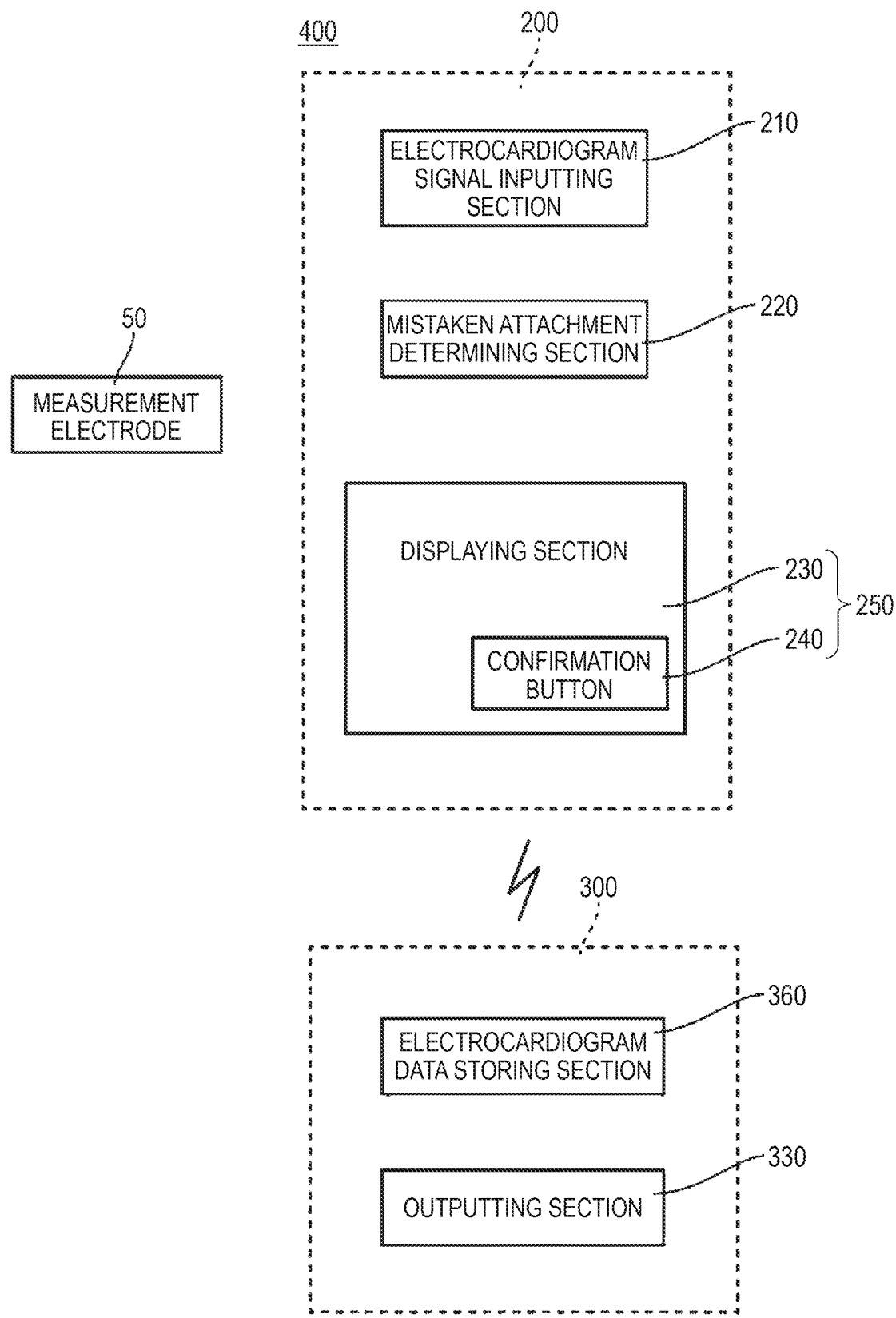
FIG. 9 is a block diagram schematically illustrating the configuration of an electrocardiogram system of Embodiment 2.

FIG. 9 is a block diagram schematically illustrating the electrocardiogram system of Embodiment 2. The electrocardiogram system 400 may include an electrocardiograph 200 and an external computer 300. The electrocardiograph 200 acquires electrocardiogram data from the measurement electrodes 50 that are attached to the subject. The external computer 300 stores the electrocardiogram data that are acquired by the electrocardiograph 200. The electrocardiograph 200 and the external computer 300 can communicate with each other. The communication may be realized by a wired connection or wireless connection. The electrocardiograph 200 is used for acquiring an electrocardiogram of the subject, and handled by an electrocardiogram technician. The external computer 300 is used for displaying the electrocardiogram that is sent from the electrocardiograph 200, and a list of test results, and handled by an interpreter such as a doctor.

The electrocardiograph 200 may include an electrocardiogram signal inputting section 210, a mistaken attachment determining section 220, a displaying section 230, and a confirmation button 240. The displaying section 230 displays the confirmation button 240. The displaying section 230 and the confirmation button 240 constitute a notifying section 250.

The functions of the electrocardiogram signal inputting section 210, the mistaken attachment determining section 220, the displaying section 230, and the confirmation button 240 are identical with those of the electrocardiogram signal inputting section 110, mistaken attachment determining section 120, displaying section 130, and confirmation button 140 of the electrocardiogram analysis apparatus 100 of Embodiment 1, respectively. If it is determined that the measurement electrodes 50 are mistakenly attached, the notifying section 250 notifies of the mistaken attachment of the measurement electrodes 50.

The external computer 300 may include an electrocardiogram data storing section 360 and an outputting section 330. In the case where there is an input indicating confirmation of the notification by the notifying section 250, the electrocardiogram data storing section 360 stores information indicating that the measurement electrodes 50 have been checked, together with the input electrocardiogram signals, and, in the case where there is not an input indicative of confirmation of the notification, stores information indicating that the measurement electrodes 50 have not been checked, together with the input electrocardiogram signals. With respect to each of the plurality of subjects, together with the electrocardiogram signals, the electrocardiogram data storing section 360 cumulatively stores information indicating that the measurement electrodes 50 have been checked, or information indicating that the measurement electrodes 50 have not been checked. When, as described above, electrocardiogram signals of the plurality of subjects, information indicative of checking and not-yet-checking of the measurement electrodes 50 are cumulatively stored, it is possible not only to see the result of checking whether mistaken attachment of the measurement electrodes 50 occurs or not, with respect to each of the subjects, but also to interpret at a glance the check results of the all subjects.

During interpretation of the electrocardiogram of the subject, the outputting section 330 displays, together with the electrocardiogram signals, information indicating that the measurement electrodes 50 have been checked, or information indicating that the measurement electrodes 50 have not been checked. Moreover, the outputting section 330 displays, in a list of test results of a plurality of subjects, information indicating that the measurement electrodes 50 have been checked, or information indicating that the measurement electrodes 50 have not been checked. Therefore, an interpreter such as a doctor can recognize through the list whether the measurement electrodes 50 of each of the subjects have been checked or not. In the list of test results, the situation where the measurement electrodes 50 have been checked, and that where the measurement electrodes 50 have not been checked are performed by displaying characters in the list, by displaying the list in different colors, or by placing marks in the list, as in Embodiment 1. Therefore, the interpreter can recognize at a glance from the list whether the measurement electrodes 50 of each of the subjects have been checked or not. The outputting section 330 may be a display device using liquid crystal or organic EL, or a printer that prints the list on a recording medium such as a pater sheet.

<Operation of Electrocardiogram System During Measurement>

The operation of the electrocardiogram system 400 during measurement is identical with the operation in the operation flowchart of the electrocardiogram analysis apparatus 100 of Embodiment 1 illustrated in FIG. 2 during measurement except that, although, in the electrocardiogram analysis apparatus 100 of Embodiment 1, information indicating "Measurement electrodes have been checked" or "Measurement electrodes have not been checked" is stored is in the electrocardiogram data storing section 160 together with the electrocardiogram signals suppled from the electrocardiogram signal inputting section 110, the electrocardiograph 200 of the electrocardiogram system 400 transmits information indicating "Measurement electrodes have been checked" or "Measurement electrodes have not been checked" together with together with the electrocardiogram signals suppled from the electrocardiogram signal inputting section 210, toward the external computer 300, and the information and the signals are stored in the electrocardiogram data storing section 360 of the external computer 300. Except the operation, the operation of the electrocardiograph 200 is identical with that of the electrocardiogram analysis apparatus 100 during measurement.

<Operation of Electrocardiogram System During Interpretation>

The operation of the electrocardiogram system 400 during interpretation is identical with the operation in the electrocardiogram analysis apparatus 100 of Embodiment 1 illustrated in FIGS. 3 and 4 during interpretation. In the case where mistaken attachment of the measurement electrodes 50 has been checked, therefore, the outputting section 330 displays or prints an image such as illustrated in FIG. 7. The interpreter such as a doctor sees the display of "Measurement electrodes have been checked" or Measurement electrodes have not been checked," and knows that the electrocardiogram 147 is a reliable electrocardiogram that is measured in a state where the measurement electrodes 50 are not mistakenly attached. The doctor can test the symptom of the patient with confidence in the electrocardiograms 147. As illustrated in FIG. 8, the outputting section 330 may display or print test results of a plurality of subjects, in the form of a list. Therefore, the interpreter can recognize at a glance from the list which one(s) of the subjects has an electrocardiogram that has been checked, or that has not yet been checked.

The electrocardiogram analysis apparatus 100 and electrocardiogram system 400 that have been exemplified in Embodiments 1 and 2 automatically determine during measurement whether the measurement electrodes 50 are mistakenly attached or not, and, if the electrodes are mistakenly attached, display the confirmation button 140 or 240 to prompt the electrocardiogram technician to check the attachment positions of the measurement electrodes 50. When the electrocardiogram technician checks that the attachment positions of the measurement electrodes 50 are correct, the electrocardiogram technician presses the confirmation button 140 or 240, and information indicating that the measurement electrodes have been checked is stored together with the electrocardiogram signals. During interpretation, the history of checking in which the electrocardiogram technician checks the attachment positions of the measurement electrodes 50 is displayed or printed together with the electrocardiogram. Therefore, it is possible to see the result of checking whether mistaken attachment of the measurement electrodes 50 occurs or not, and the interpreter can test the symptom of the patient with confidence in the electrocardiogram.

Although the electrocardiogram analysis apparatus 100 and electrocardiogram system 400 of the embodiments have been described above, the technical scope of the presently disclosed subject matter is not limited to the description of the embodiments. For example, an apparatus that is configured so that the result of checking whether the attachment positions of the measurement electrodes 50 are mistaken or not is stored, and the check result is enabled to be seen thereafter is included within the technical scope of the presently disclosed subject matter.

According to the electrocardiogram analysis apparatus and electrocardiogram system of the presently disclosed subject matter, an interpreter can see a result of checking whether measurement electrodes have been mistakenly attached or not. When seeing a measured electrocardiogram, an interpreter can know that the measurement has been performed while attaching the measurement electrodes to correct locations. Therefore, an interpreter can test the symptom of the subject while trusting the electrocardiogram, and the reliability of the test is improved.

What is claimed is:

1. An electrocardiogram analysis apparatus comprising:
   an electrocardiogram signal inputting section to which electrocardiogram signals of a plurality of measurement electrodes that are attached to a subject are input;
   a mistaken attachment determining section which, by using the input electrocardiogram signals, is configured to determine whether the measurement electrodes are mistakenly attached or not;
   an outputting section which, if it is determined that the measurement electrodes are mistakenly attached, is configured to notify of mistaken attachment of the measurement electrodes and to display a confirmation button that when pressed provides an indication of confirmation of the notification; and
   an electrocardiogram data storing section which, in a case where the indication of confirmation of the notification is provided, is configured to store information indicating that the measurement electrodes have been checked, together with the input electrocardiogram signals, and, in a case where the indication of confirmation of the notification is not provided, is configured to store information indicating that the measurement electrodes have not been checked, together with the input electrocardiogram signals,
   wherein the outputting section is configured to determine whether a user has checked the mistaken attachment of the measurement electrodes based on the indication of confirmation of the notification provided when the confirmation button is pressed, and
   wherein the outputting section displays, for the subject, the information indicating that the measurement electrodes have been checked or the information indicating that the measurement electrodes have not been checked, based on the determination.

2. The electrocardiogram analysis apparatus according to claim 1, wherein, with respect to each of a plurality of subjects, the electrocardiogram data storing section is configured to cumulatively store information indicating that the measurement electrodes have been checked, or information indicating that the measurement electrodes have not been checked, together with the electrocardiogram signals.

3. The electrocardiogram analysis apparatus according to claim 1, wherein the outputting section further outputs the information indicating that the measurement electrodes have been checked, or the information indicating that the measurement electrodes have not been checked, together with the electrocardiogram signals.

4. The electrocardiogram analysis apparatus according to claim 2, wherein the outputting section further displays the information indicating that the measurement electrodes have been checked, or the information indicating that the measurement electrodes have not been checked, in a list of test results of the plurality of subjects.

5. The electrocardiogram analysis apparatus according to claim 4, wherein the display of the information indicating that the measurement electrodes have been checked, or the information indicating that the measurement electrodes have not been checked, in the list of test results is performed by displaying a character in the list, by displaying the list in different colors, or by placing a mark in the list.

6. An electrocardiogram system which includes an electrocardiograph that acquires electrocardiogram data of a subject, and an external computer that stores the electrocardiogram data acquired by the electrocardiograph, and in which the electrocardiograph and the external computer are communicable with each other, wherein
   the electrocardiograph includes:
      an electrocardiogram signal inputting section to which electrocardiogram signals of a plurality of measurement electrodes that are attached to the subject are input;
      a mistaken attachment determining section which, by using the input electrocardiogram signals, is configured to determine whether the measurement electrodes are mistakenly attached or not; and
      a notifying section which, if it is determined that the measurement electrodes are mistakenly attached, is configured to notify of mistaken attachment of the measurement electrodes and to display a confirmation button that when pressed provides an indication of confirmation of the notification, and
   the external computer includes:
      an electrocardiogram data storing section which, in a case where the indication of confirmation of the notification is provided, is configured to store information indicating that the measurement electrodes have been checked, together with the input electrocardiogram signals, and, in a case where the indication of confirmation of the notification is not provided, is configured to store information indicating that the measurement electrodes have not been checked, together with the input electrocardiogram signals; and
      an outputting section that is configured to determine whether a user has checked the mistaken attachment of the measurement electrodes based on the indication of confirmation of the notification provided when the confirmation button is pressed, and to output, for the subject, the information indicating that the measurement electrodes have been checked, or the information indicating that the measurement electrodes have not been checked, together with the electrocardiogram signals.

7. The electrocardiogram system according to claim 6, wherein, with respect to each of a plurality of subjects, the electrocardiogram data storing section is configured to cumulatively store data of the information indicating that the measurement electrodes have been checked, or data of the information indicating that the measurement electrodes have not been checked, together with the electrocardiogram signals.

8. The electrocardiogram system according to claim 7, wherein the outputting section displays the information indicating that the measurement electrodes have been checked, or the information indicating that the measurement electrodes have not been checked, in a list of test results of the plurality of subjects.

9. The electrocardiogram system according to claim 8, wherein the display of the information indicating that the measurement electrodes have been checked, or the information indicating that the measurement electrodes have not been checked, in the list of test results is performed by displaying a character in the list, by displaying the list in different colors, or by placing a mark in the list.

* * * * *